United States Patent [19]

Bessman et al.

[11] 4,431,004
[45] Feb. 14, 1984

[54] IMPLANTABLE GLUCOSE SENSOR

[76] Inventors: Samuel P. Bessman, 2025 Zonal Ave., Los Angeles, Calif. 90033; Ennis C. Layne, 9128 Huntington Dr., San Gabriel, Calif. 91775; Lyell J. Thomas, 1900 Pelican Ave., San Pedro, Calif. 90732

[21] Appl. No.: 315,282

[22] Filed: Oct. 27, 1981

[51] Int. Cl.³ .............................................. A61B 5/00
[52] U.S. Cl. .................................. 128/635; 128/632; 204/195 B
[58] Field of Search ............................. 128/632, 635; 204/195 B

[56] References Cited

U.S. PATENT DOCUMENTS

| | | | |
|---|---|---|---|
| 3,770,607 | 11/1973 | Williams | 128/635 X |
| 3,920,969 | 11/1975 | Berglas | 204/195 B X |
| 4,240,438 | 12/1980 | Updike et al. | 128/635 |
| 4,301,807 | 11/1981 | Mentelos | 128/635 |

OTHER PUBLICATIONS

Kondo et al., "Trial of New Vessel Access Type Glucose Sensor for Implant. Art. Pancreas in Vivo"; Trans. Am. Soc. Artif. Intern. Organs, vol. XXVII, 1981, pp. 250–252.
Pagurek et al., "Adaptive Control of Human Glucose-Regulatory System"; Med. and Biol. Engr., vol. 10, No. 6, 11-1972, pp. 752–761.
Chang et al., "Validation and Bidengr. Aspects of an Implant. Glucose Sensor"; Trans. Am. Soc. Artif. Int. Organs; vol. XIX, 1973, pp. 352–360.
Chua et al., "Plasma Glucose Measurement with the Yellow Springs Glucose Analyzer"; Clin. Chem. 24/1, pp. 150–152, 1978.
Danielsson et al.; "Use of an Enzyme Thermistor in Continuous Measurements and Enzyme Reactor Control"; Biotechnology and Bioengineering, vol. 21, pp. 1749–1766, 1979.
Bessman et al.; "Implantation of a Closed Loop Artificial Beta Cell in Dogs"; Trans. Am. Soc. Artif. Inter. Organs; vol. 28, 1981, pp. 7–18.
Mahler et al., "Kinetics of Enzyme-Catalyzed Reactions"; Biol. Chem.; 1966, pp. 237–241.
Clark et al.; "Differential Anodic Enzyme Polarography for the Measurement of Glucose"; Adv. Exp. Med. Biol.; 37A, pp. 127–133, 1973.
Updike et al., "The Enzyme Electrode"; Nature, vol. 214, 6-1967, pp. 986–988.
Wingard et al., "Immobilized Enzyme Electrodes for the Potentiometric Measurement of Glucose Concentration"; Journ. of Biomed. Mat'ls Res., vol. 13, pp. 921–935, 1979.
Layne et al.; "Continuous Extracorporeal Monitoring of Animal Blood Using the Glucose Electrode"; Diabetes 25, pp. 81–89, 2-1976.

Primary Examiner—Kyle L. Howell
Assistant Examiner—Angela D. Sykes
Attorney, Agent, or Firm—Fidelman, Wolffe & Waldron

[57] ABSTRACT

A method and apparatus for more accurate measurements of the glucose content in body fuids by sensing the absolute level of oxygen concentration in the fluid and correcting the output differential measurement indicative of the glucose content in the fluid according to the absolute level of oxygen.

In the two electrode systems known to the art, the unaltered oxygen electrode of the electrode pair may be employed to read the absolute level of oxygen concentration and in addition, function to establish the difference in oxygen concentration caused by glucose oxidation.

In view of the fact that temperature may vary, a thermistor may be included in the electrode system to make temperature corrections for reason that the absolute oxygen reading from either a polarographic or galvanic oxygen electrode is extremely sensitive to temperature and the rate of glucose oxidation is temperature sensitive.

8 Claims, 5 Drawing Figures

IMPLANTABLE GLUCOSE SENSOR

This invention relates to a glucose sensor, and, in particular, to an implantable glucose sensor.

BACKGROUND OF THE INVENTION

Measurement of glucose in solution in body fluids is usually carried out by measuring the consequence of oxidation of the glucose in the body fluid. This oxidation may be catalyzed by an enzyme, e.g., glucose oxidase.

The glucose oxidase reaction is as follows:

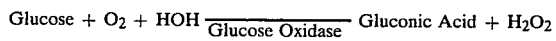

$$\text{Glucose} + O_2 + \text{HOH} \xrightarrow{\text{Glucose Oxidase}} \text{Gluconic Acid} + H_2O_2$$

Several configurations of electrodes using this reaction which might be applied to body fluids have been suggested to the art.

According to a suggestion made by Clark et al., a polarographic oxygen electrode is placed behind a chamber filled with a solution of glucose oxidase. The outer wall of the chamber is permeable to glucose and oxygen, and the wall of the chamber facing the oxygen electrode is permeable only to oxygen. When a glucose solution is applied to the outer membrane, the glucose oxidase reaction consumes oxygen, diminishing the reading of the oxygen electrode as some function of the glucose concentration. For details of this suggestion, see L. C. Clark, Jr. and E. W. Clark. "Differential Anodic Enzyme Polarography for the Measurement of Glucose", Adv. Exp. Med. Biol. 37A, 127–133 (1973).

According to a suggestion made by Updike and Hicks, two polarographic oxygen electrodes are placed behind two cylinders of gel. One cylinder of gel contains entrapped vacuoles of glucose oxidase solution and the other acts as a control. The amount of glucose in a solution is determined as a function of the difference in the reading of the two electrodes, only one of which is affected by the presence of glucose in a similar manner to the Clark electrode. See Updike, S. J. and Hicks, G. P. "The enzyme electrode, a miniature chemical transducer using immobilized enzyme activity". Nature 214, 986 (1967) and also Wingard, Jr., L. B., Schiller, J. G., Wolfson, Jr., S. K., Liu, C. C., Drash, A. L. and Yao, S. J. "Immobilized Enzyme Electrodes for the Potentiometric Measurement of Glucose Concentration". J. Biomed. Mat. Res. 13, 921–935, (1979).

Another suggestion is for a differential electrode using two galvanic oxygen cells, one of which is a reference and the other covered by a plastic membrane containing covalently bonded glucose oxidase in a closed loop "artificial beta cell" as well as for other measurements. See Layne, E. C., Schultz, R. D., Thomas, Jr., L. J., Slama, G., Sayler, D. F. and Bessman, S. P. "Continuous Extracorporeal Monitoring of Animal Blood Using the Glucose Electrode". Diabetes 25, 81–89 (1976).

Still another suggestion is for an electrode which uses glucose oxidase to form peroxide which is read directly using a polarographic cell. See Chua, K. S. and Tan, F., "Plasma Glucose Measurement with the Yellow Springs Glucose Analyzer". Clin. Chem. 24, 150–152 (1978).

One suggested measurement for glucose relies on heat generated by the above reaction. Suggested has been an electrode which measures temperature of the glucose oxidase using a very sensitive thermistor covered with a layer of glucose oxidase. See Danielsson, B., Mattiason, B., Karlsson, R. and Winquist, F. "Biotechnology and Bioengineering," Vol. XXI, Pg. 1749–1766 (1979) John Wiley and Sons, Inc.

One way or another, all of the suggestions made heretofore, such as those alluded to above, assume that the actual level of dissolved oxygen in the body fluid is of no significant consequence to the glucose measurement since only the changes in one reactant or another, as indicated by oxygen utilization or formation of peroxide, by generation of heat, or of gluconic acid are indicative of glucose concentration.

However, availability of oxygen for reaction with glucose, i.e., actual oxygen concentration in the body fluid is a limiting factor for the glucose oxidation reaction. Yet, as has been pointed out above, the art has not heretofore accounted for limitations imposed by availability of oxygen on the electrode systems which depend on glucose oxidation for measuring glucose content in body fluid.

THE INVENTION

The present invention provides a method and apparatus for more accurate measurements of the glucose content in body fluids by sensing the absolute level of oxygen concentration in the fluid and correcting the output differential measurement indicative of the glucose content in the fluid according to the absolute level of oxygen.

In the two electrode systems known to the art, the unaltered oxygen electrode of the electrode pair may be employed and preferably is employed to read the absolute level of oxygen concentration in addition to functioning to establish the difference in oxygen concentration caused by glucose oxidation.

In view of the fact that temperature may vary in the body, a thermistor should be included in the electrode system to make temperature corrections for two reasons—first, the absolute oxygen reading from either a polarographic or galvanic oxygen electrode is extremely sensitive to temperature—second, the rate of glucose oxidation is temperature sensitive. Appropriate means for corrections of electrode readings must therefore be incorporated in the electrode system.

DISCUSSION OF THE INVENTION

For further understanding of this invention, reference is now made to the attached drawings wherein:

FIG. 5 is a circuit diagram for an exemplary embodiment of this invention.

FIG. 1 illustrates the measurement errors which may arise because the oxygen signal differential ususally taken as the measure of glucose concentration varies with the initial oxygen concentration in the fluid being tested.

Figure 1:
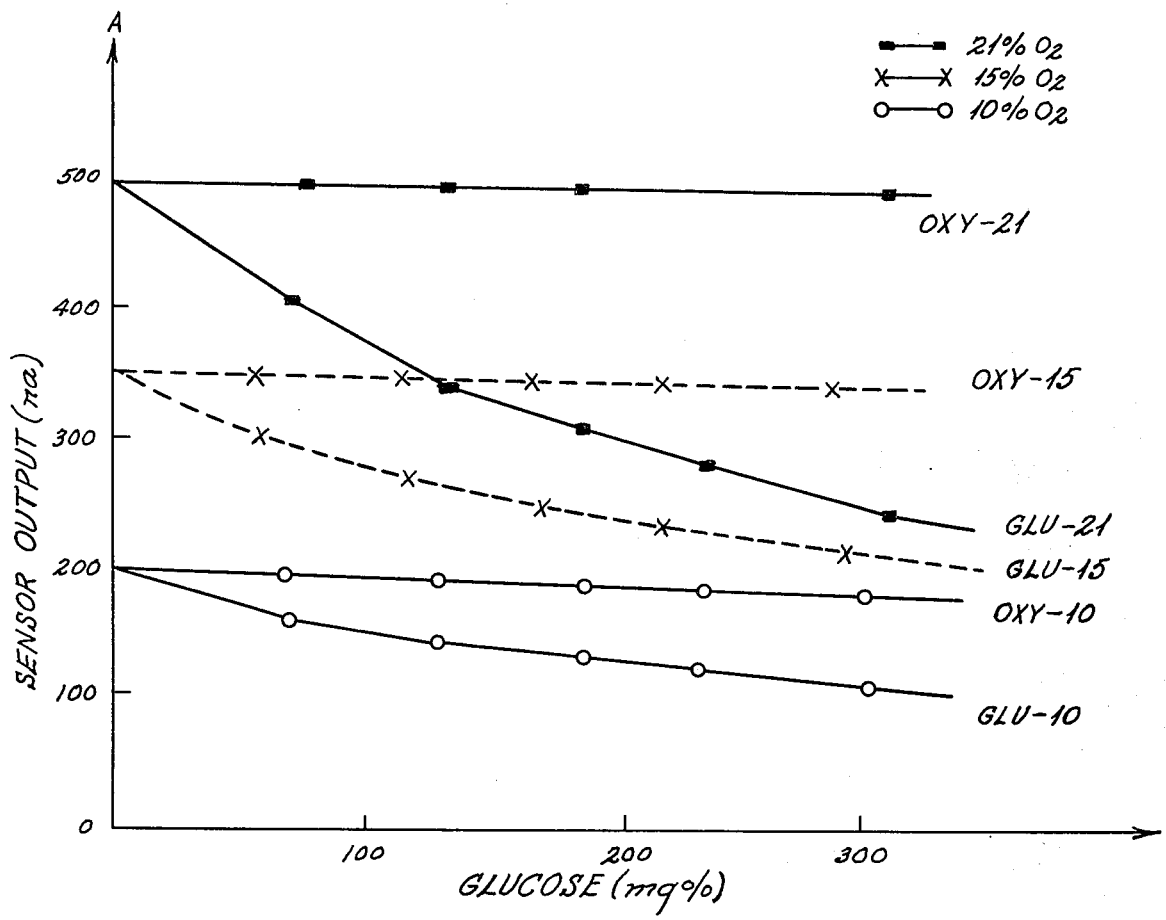
FIG. 1 is a graph illustrating sensor current output plotted against glucose content for body fluids of varying oxygen levels.

The following test procedure generated the data graphed on FIG. 1.

The test apparatus consisted of a 15 ml water jacketed test chamber with the water pumped into the jacket from a thermostatically temperature controlled bath. Provision existed for adjusting the temperature of the bath and therefore of the test chamber.

The test chamber was fitted with a multi-ported cap (four ports) for entrance of gas, exit of gas, exit of wires to sensor and a rubber stoppered access port for addition of glucose solution. The chamber was equipped with a magnetic stirrer.

A known volume of water (10 to 15 ml) was added to the chamber and the galvanic glucose-oxygen sensor submerged. A commercial mixture of oxygen-nitrogen was vigorously bubbled into the fluid at the bottom of the chamber exiting at the top.

Glucose concentration was altered by the successive addition of 50 μl aliquots of concentrated glucose solution to the chamber. After mixing, a 50 μl aliquot of the chamber contents was removed for chemical analysis.

Sensor current was measured as voltage drop across a 20,000 Ohm load resistor. At each measurement point the sensor was allowed to equilibrate, evidenced by constant current output for at least 20 minutes.

Looking now to FIG. 1, it may be seen that the oxygen electrode provides a steady level output in Nano amperes regardless of variations in glucose concentration. However, the output of the oxygen electrode depends on the oxygen concentration in the oxygen-nitrogen mixture, as may be seen by the parallel horizontal lines for the different 10%, 15% and 21% oxygen content levels. As may be seen from the curves plotted in FIG. 1, the output of the glucose electrode under the different oxygen concentration conditions is clearly some function of the oxygen concentration as well as of the glucose concentration. An output of 300 na from the glucose electrode represents a glucose concentration of 55 mg% in 15% oxygen, but 200 mg% at 21% oxygen.

Figure 2:
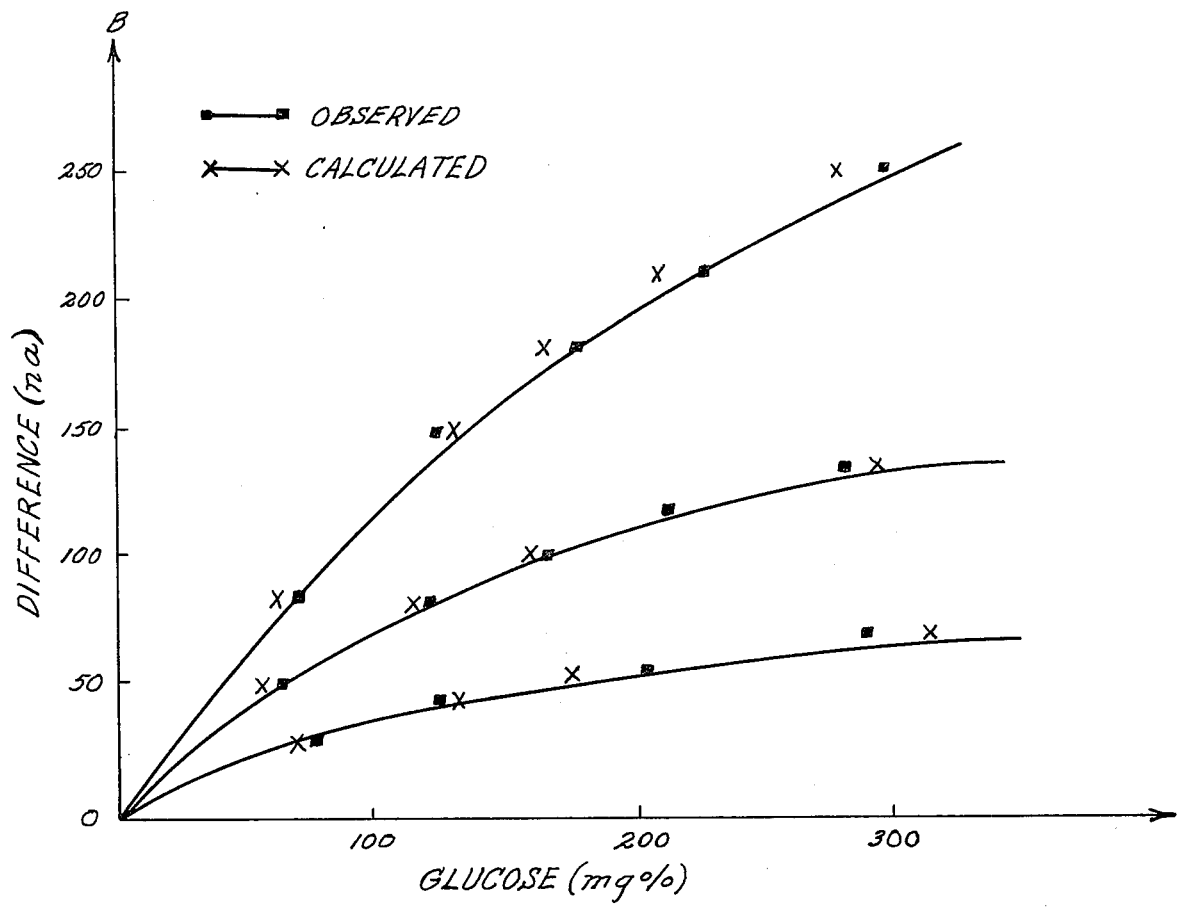
FIG. 2 is a graph illustrating the current output difference between an electrode pair plotted against glucose content at varying oxygen levels.

That the differential in electrode output from the two electrodes is not representative only of the glucose concentration may be seen on FIG. 2, whereon the differences in output at 10%, 15% and 21% oxygen in the oxygen-nitrogen mixture are plotted against glucose concentration.

The reading for 200 mg% glucose is about 50 na when oxygen concentration is 10%, about 100 na when oxygen concentration is 15%, and about 200 na when oxygen concentration is about 21%. Conversely, a differential in output of about 75 na could therefore be indicative of a glucose concentration somewhere between 55 to 200 mg% and a more exact estimate of glucose concentration requires ascertaining ambient oxygen concentration more closely than the about 5%-15% range that exists in body fluids.

The wide range of uncertainty regarding glucose concentration shown by the data plotted on FIGS. 1 and 2 presents a serious problem in treatment of diabetics. For example, if a dual electrode device were used to sense arterial blood glucose level in an animal or human patient, in face of arterial blood oxygen variations between 21% and 10% oxygen depending upon respiration efficiency, interpretation of the 50 na sensor signal as 200 mg% glucose would indicate the need to administer insulin, whereas interpretation of the sensor signal as 55 mg% glucose makes the reading an absolute contraindication for insulin administration.

Since the differential output is demonstrated by FIG. 2 to be some function of the oxygen concentration, conversion of the differential output into a more accurate measurement for glucose concentraton should be made, and by practice of this invention the differential output is corrected for oxygen concentration. Oxygen concentration may be read by a reference electrode, or in preferred embodiments of this invention on the fly, so to speak, by the (unaltered) oxygen electrode of the oxygen electrode-glucose oxidase containing electrode pair. The additional information as to ambient oxygen concentration from the oxygen sensitive electrode(s) employed is coupled with the difference in electrical output from the glucose sensitive electrode and the oxygen electrode for measurement of glucose concentration as a function of the two outputs.

The outputs from a glucose oxidase containing electrode and the oxygen electrode(s) are sufficient to estimate glucose concentration to meaningful accuracy at a constant temperature. Mathematical techniques are available empirically or theoretically to generate functions which, for example, fit the data provided on FIGS. 1 and 2, to meaningful accuracy within the precision of the data. For example, the reciprocal of the current difference between the two sensors has roughly a linear relation to the reciprocal of the glucose concentration. However, the constants of linearity are different for each oxygen concentration. The actual function used to correct for oxygen concentration employed may be selected for simplicity, accuracy or convenience.

In making the correction, data from the oxygen-only sensor is used to develop the difference signal and then either is used again or is taken from the added (control) oxygen electrode for correcting the difference signal so as to balance out the effect of the oxygen concentration level upon the activity of the glucose oxidase enzyme.

As an example, FIG. 2 illustrates one calculated correction which has less than a 10% error from the observed results over the clinically interesting range of glucose concentration from 50 to 150 mg % glucose under conditions wherein the ambient oxygen concentration was 21%, 15% and 10%.

The experimental data plotted on FIG. 2 (solid squares) are the current differences measured between the oxygen-sensitive output (Ro) and the glucose-sensitive output (Rg). This difference (D) when plotted against glucose concentration (G) yields a hypothetic function typical of enzyme kinetics and the double-reciprocal plot is roughly linear. Thus:

$$1/D = B_1/G + A_1 \qquad (1)$$

Where $B_1$ is the slope, $A_1$ the intercept and $D = Ro - Rg$. At 21% oxygen $A_1 = 1.79 \times 10^{-3}$ and $B_1 = 0.637$. For any given difference between oxygen current (Ro) and glucose current ($R_g$) measured at 21% oxygen, the corresponding glucose concentration can be calculated from equation (1).

$$G_{(mg\%)} = B_1/((1/D - A_1)) \qquad (2)$$

Similar linear expressions can be derived for 15% and 10% oxygen but with different slopes and intercepts. It is found empirically that the slopes and intercepts vary linearly with the logarithm of the oxygen reading (ro). Thus:

$$A_1 = A_2 + B_2 \log Ro \qquad (3)$$

$$B_1 = (A_3 + B_3 \log R1)/A_1 \qquad (4)$$

$A_2$, $B_2$, $A_3$ and $B_3$ are empirically determined for each sensor. In the instance of the experimental data test results plotted in FIGS. 1 and 2:

$$A_2 = 0.3955$$

$$B_2 = 1.398 \times 10^{-2}$$

$$A_3 = 0.5287$$

$$B_3 = 1.920 \times 10^{-2}$$

The calculated results (x—x) plotted on FIG. 2 were obtained by deriving $A_1$ and $B_1$ from equations 3 and 4 utilizing the reading of the oxygen sensor. $A_1$ and $B_1$ are then employed in equation (2) to calculate glucose concentration from the differences observed between the oxygen and the glucose sensor.

In addition to the graphic presentation of experimental and calculated results plotted on FIG. 2, the experimental and calculated results have been tabulated and form part of the data hereinafter provided in Table I.

The glucose oxidase glucose sensor is temperature sensitive. For example, Table I shows also representative measurements taken over the temperature range from room-temperature to body temperature. Output of the oxygen sensitive area ($R_o$) varies from 218 to 523 na and the glucose sensitive area varies also. The enzyme glucose oxidase is known to be temperature sensitive. Estimation of variations in glucose concentration with glucose sensor devices requires adjustment for temperature, if temperature variation between successive measurements are expected to occur, as for instance, between calibration of a device at ambient temperature, but measurements at body temperature.

cose oxidase activity to some standard reference condition. It is not required that the temperature conditions of use and calibration or reference conditions be the same. The correction function may be obtained from theoretical considerations or from an empirical fit to the sensor output versus T° curve. Here, too, the function may be selected for simplicity, accuracy or convenience. In Table I is shown an example of such a correction.

In the exemplary data tabulated below in Table I, the sensor readings observed (Col. 1 and 2) were corrected to 37° C. by the relationship $$R_{36} = ((8.929 - 2.17 (\ln T)) R_T \tag{5}$$

Where T is the centigrade temperature of observation and $R_T$ is the sensor reading at that temperature. This relation was selected for convenience and has up to about a 10% error.

The sensor readings were then utilized in equation 2 to calculate an intermediate value for glucose concentration (Col. 4, Table I) which was corrected for the effect of temperature on the enzyme activity by the equation $$\text{Glucose } (37) = G_t \ln (37 - T) \tag{6}$$

Where
 $G_T$ is the intermediate calculated glucose value
 T is the temperature of observation
 In the special case where T° = 37°, i.e., body temperature, no correction is necessary. To repeat, the function (equation 6) and the reference temperature (37°) were selected for convenience and to illustrate practice of this invention.

TABLE I

GLUCOSE CONCENTRATION VS. SENSOR OUTPUT AT DIFFERENT TEMPERATURES

| | | OBSERVED | | OXYGEN READING CORRECTED TO 37° C.[3] | | CALCULATED Glucose[4] | TEMPERATURE CORRECTED[5] GLUCOSE |
|---|---|---|---|---|---|---|---|
| Temp | Glucose | $R_g$[1] | $R_o$[2] | $37_{R_g}$ | $37_{R_o}$ | $G_0$ (mg %) | $G_{ot}$ (mg %) |
| 37 | 50 | 400 | 523 | 400 | 523 | 65.2 | 65.2 |
| | 100 | 335 | 514 | 335 | 514 | 112 | 112 |
| | 150 | 283 | 500 | 283 | 500 | 162 | 162 |
| | 200 | 262 | 497 | 263 | 497 | 186 | 186 |
| 29 | 50 | 273 | 308 | 441 | 498 | 26.1 | 54 |
| | 100 | 238 | 301 | 385 | 487 | 53.7 | 112 |
| | 200 | 196 | 301 | 318 | 487 | 107 | 222 |
| 23.3 | 50 | 205 | 218 | 418 | 445 | 13.9 | 36.3 |
| | 100 | 186 | 218 | 378 | 445 | 38 | 99.5 |
| | 150 | 167 | 220 | 340 | 449 | 67.4 | 176 |
| | 200 | 154 | 220 | 313 | 449 | 89.1 | 233 |

Figure 3:
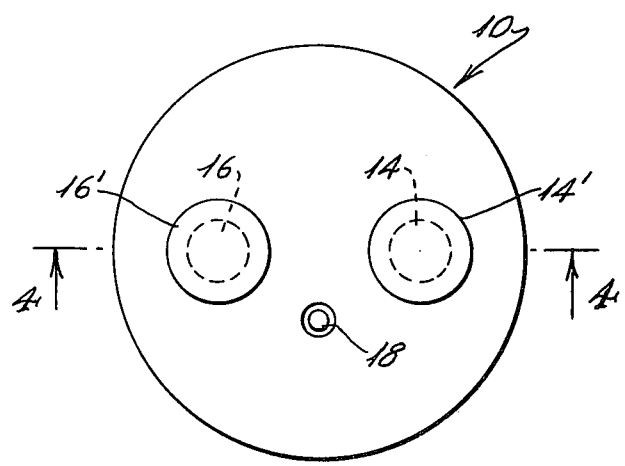
FIG. 3 is a plan view of an electrode pair configuration.
Figure 4:
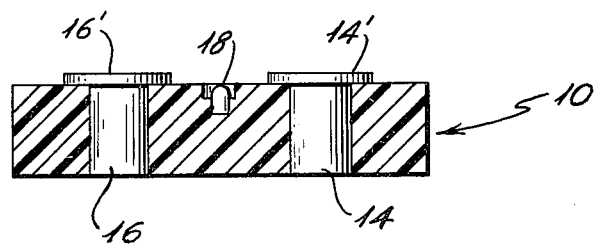
FIG. 4 is a side section view along line 4—4 of FIG. 3.
Figure 3:
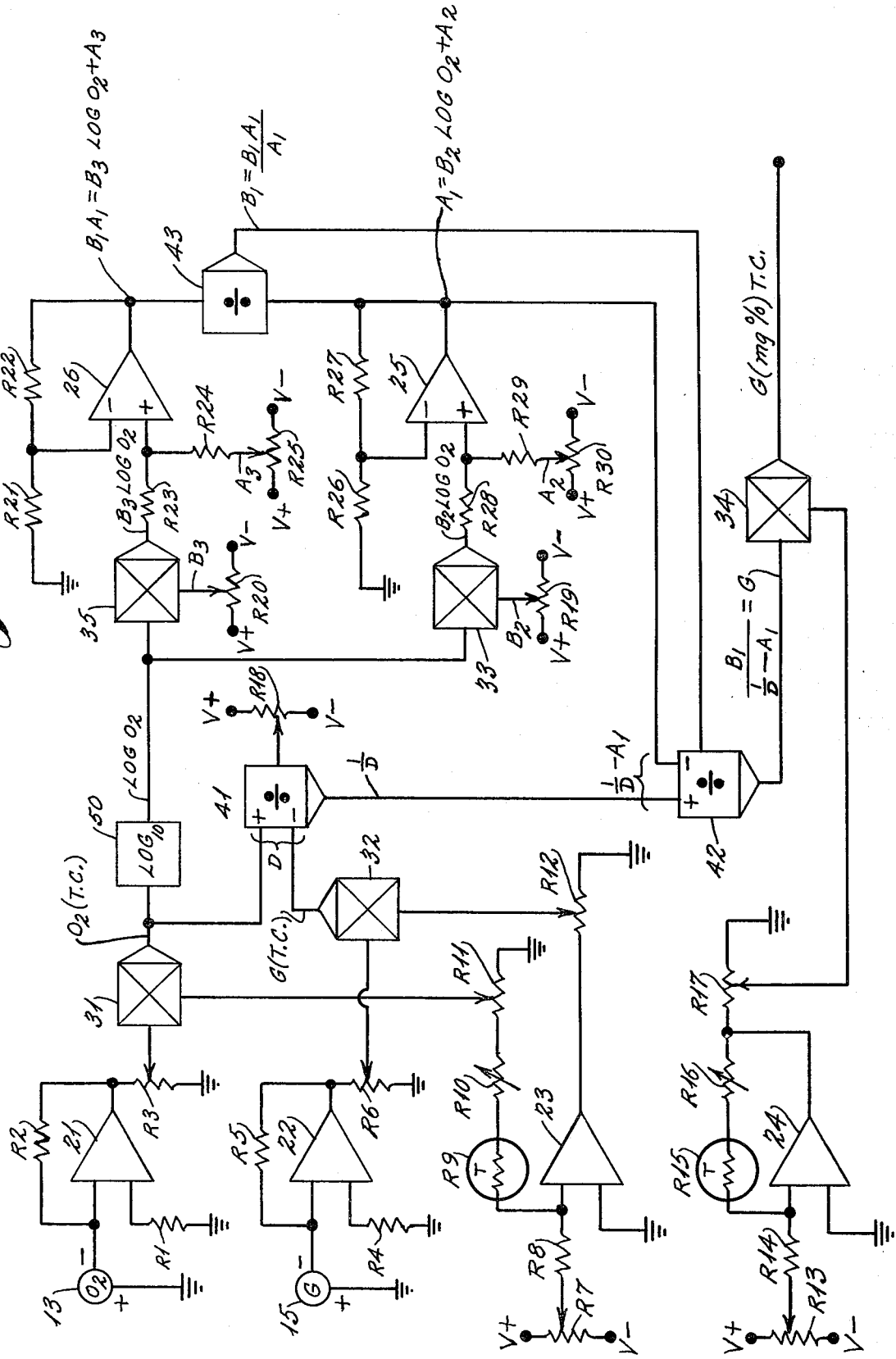

[1] $R_g$ = output of glucose sensitive area
[2] $R_o$ = output of oxygen sensitive area at 21% ambient oxygen
[3] $37_{R_x}$ = [8.929 − 5.0 (log $T_c$)] $R_x$ where x = g or o and $T_c$ = temperature in centigrade degrees
[4] Calculated as for FIG. 2 $G_{ot} = G_o \ln (37 - T_c)$ A preferred embodiment of this invention, i.e., the device illustrated by FIGS. 3 and 4, employs a glucose sensor 10, which contains a glucose sensitive area 14, an oxygen sensitive area 16 and a means for sensing ambient temperature. The temperature sensor might, for example, be the thermistor 18, as is illustrated, or alternatively a thermometer, or a pressure sensitive device, a heated or cooled reference area, or a volume sensitive device, or other known to the art sensor means suited to measure temperature changes.

Output of the temperature sensor 18 is used to correct the glucose sensitive, oxygen sensitive output and glu- In summary, the glucose sensors contemplated for practice of this invention, may be used as an implantable or external sensor of glucose based on glucose oxidase utilization of oxygen in the presence of glucose. It is required that the sensor have an oxygen sensitive area in addition to a glucose sensitive one, and desirably an independent temperature sensitive output. Corrections for temperature and oxygen concentration to the sensor output signal are applied by analog or digital means, which per se are known to the art, so as to make the sensor output an accurate reading of glucose concentration.

The sensor device may be calibrated under conditions different from use or from reference conditions. For example, a sensor intended for use implanted in the human body at 37° C. and 3% oxygen can be calibrated at room temperature and atmospheric (20%) oxygen.

Practice of this invention is not limited to the sensors herein described nor to the sensor measurement modes herein described.

Another embodiment of the principles and practice of this invention may be in the polarographic measurement of peroxide generation by glucose oxidase as the glucose reactive area of an electrode as has been suggested by Chua et al. supra. In such system, the net peroxide formed at a particular glucose concentration is also a function of the oxygen concentration and temperature and for accuracy must be corrected, for example, by including an oxygen sensitive area and appropriate known-to-the-art circuitry. Although correction for oxygen concentration is not absolutely necessary when the electrode is used in air or in any environment higher than 150 mm pO2, at the low and variable pO2 encountered even in flowing blood the separate correction herein described using a reference oxygen measurement should be made for accurate measurement of glucose concentration.

Another embodiment of practice of this invention may be in the measurement of the heat capacity of the reaction of glucose oxidase with glucose as has been suggested by Danielson et al. (supra). The reference temperature is read from a thermal sensitive area and the glucose sensitive area is an equivalent thermal sensitive area with attached glucose oxidase. In this instance the concentration of glucose is read as a function of the temperature differential between the reference and the glucose sensitive areas. This thermal reading for glucose concentration may be corrected as has been described above according to the temperature corrected oxygen value reading from an oxygen sensitive area, with appropriate known-to-the-art circuitry.

Correction for oxygen concentration as described herein may be applied to all glucose electrodes dependent on oxidation, e.g., fuel cells as suggested by Bessman, S. P. and Schultz, R. D. "Sugar Electrode Sensor for the 'Artificial Pancreas'". Horm. Metab. Res. 4,413–417 (1972). For accurate measurement of glucose concentration, it is not enough to use a reference fuel cell and measure differences alone. As long as the sensing mechanism is not exposed to an excess of oxygen, which means in all environments within the body including arterial blood, every sensor which depends on oxidation is dependent also upon the oxygen tension.

For further understanding of this invention and the practice thereof, the circuit diagram for one preferred mode of this invention has been illustrated on FIG. 5 and is hereinafter described.

Referring now to FIG. 5, it may be seen that currents from oxygen electrode 13 and glucose electrode 15 are converted to oxygen and glucose voltages, respectively, by amplifiers 21 and 22. These oxygen and glucose voltages are temperature compensated by outputs from amplifier 23. For instance, the oxygen output voltage of amplifier 21 (via potentiometer R3) and a temperature compensating output of amplifier 23 (via potentiometer R11) are multiplied in multiplier 31 to yield a temperature corrected output voltage, $O_2$(T.C.), as indicated at the output of multiplier 31. Correspondingly, the glucose voltage output of amplifier 22 (via potentiometer R6) and a temperature compensating output from amplifier 23 (via a potentiometer R12) are multiplied in multiplier 32 to yield a temperature compensated glucose voltage, G. (T.C.), as indicated at the output of multiplier 32. This temperature correction occurs due to thermistor R9, appropriately trimmed by R10, causing the output of amplifier 23 to vary inversely to the outputs of amplifiers 21 and 22 (oxygen sensitive current only) with temperature. The temperature corrected glucose and oxygen voltages are subtracted at the differential denominator input of divider 41 and divided into a voltage arbitrarily set by potentiometer R18. The output from potentiometer R18 may be made equal to unity, for convenient subsequent calculation, by setting the potentiometers R19, R20, R25 and R30 (outputs of which correspond to constants $B_2$, $B_3$, $A_3$ and $A_2$). Accordingly, the output from divider 41 will be 1/D, (from the left side of equation[1]).

The derived constants $A_1$ and $B_1$ are obtained, with the notation (T.C.) omitted from the remaining computation for convenience, as follows: The output of multiplier 31 is converted to its logarithm, base 10, by LOG module 50 to yield LOG $O_2$. To compute $A_1$, the output from this LOG module 50 is, in turn, multiplied in multiplier 33 by the voltage generated at R19 to yield $B_2$ LOG $O_2$. This output from multiplier 33 is then added to the voltage generated at R30, by amplifier 25, to yield $A_1 = B_2$ LOG $O_2 + A_2$ (equation 3). In a similar manner, $A_1B_1$ is computed by multiplying the output of LOG module 50, in multiplier 35, by the voltage generated at R20 to yield $B_3$ LOG $O_2$ which, in turn, is added to the voltage generated at R25, in amplifier 26, to yield $A_1B_1 = B_3$ LOG $O_2 + A_3$ (a form of equation 4). This output from amplifier 26 ($B_1A_1$) is then divided, in divider 43, by the output of amplifier 25 ($A_1$) to yield $B_1$. The output from divider 41 (1/D) is applied to the positive side of the differential denominator input of divider 42 and the output from amplifier 25 (derived constant $A_1$) is applied to the negative side of this denominator input, while the output of divider 43 (derived constant $B_1$) is fed to the numerator input of divider 42. Thus, the output of divider 42 (equation 2) is the value of measured glucose concentration correction for oxygen concentration. Temperature correction for glucose oxyidaze enzyme activity is accomplished, similar to the previous temperature correction, at multiplier 35, by appropriately trimming the output of amplifier 24 with potentiometer R16. The output of amplifier 24 is fed to one input of multiplier 34 and that of divider 42 is fed to the other input of multiplier 34, yielding an output which gives the measured glucose sensitive current of the sensor corrected to a specified temperature and oxygen concentration.

Typical active components for a prototype include the following: LF355FET high impedance input operational amplifiers for components 21–24; LM741 operational amplifiers for components 25 and 26; AD532 integrated circuit multipliers for components 31–35; AD535 integrated circuit dividers for components 41–43; and AD755 LOG antilog amplifier for LOG module 50. Thermistors R9 and R15 may be YSI #44004 Thermistors rated 2.2KΩ at 25° C.

We claim:

1. In a method for measuring the glucose content in body fluids by ascertaining the output differential between a pair of adjacent oxygen sensors placed into contact with body fluids, one of said oxygen sensors being unaltered, the other of said oxygen sensors containing glucose oxidase positioned between said other sensor and body fluids placed into contact with said other sensor, whereby the sensor pair measures an oxygen content differential in body fluids placed into contact with the sensor pair, said measured differential corresponding to the extent oxygen in the body fluids has been removed by oxidation of glucose in the body fluids, being thereby a reading for the glucose content in the body fluids, the improvement which comprises measuring the level of oxygen in the body fluids and adjusting said measured differential according to the level of oxygen, whereby the adjusted measured differential constitutes a more accurate reading for the glucose content in the body fluids.

2. The method of claim 1 wherein said improvement further comprises measuring the level of oxygen in the body with the unaltered oxygen sensor.

3. The method of claim 1 including adjusting said measured differential according to the temperature at which measurement is made.

4. The method of claim 1 wherein said sensors are oxygen electrodes and their adjusted current output differential constitutes the glucose content measurement.

5. In a glucose sensor for measuring the glucose content in body fluids comprising a pair of adjacent oxygen sensors, one of said oxygen sensors being unaltered and the other of said oxygen sensors formed into a glucose sensor by inclusion therewith of glucose oxidase positioned between said other sensor and any body fluids placed into contact with said other sensor, said pair of sensors being interconnected to provide an output differential that constitutes a reading for the glucose content in body fluids placed in contact with the pair of sensors, the improvement which comprises having said glucose sensor both to measure the oxygen concentration in body fluids placed in contact with the pair of sensors and to adjust the said output differential of the sensor pair according to the oxygen concentration, whereby a more accurate reading for glucose content is provided.

6. The glucose sensor of claim 5 further comprising the unaltered oxygen sensor providing said measurement of the oxygen concentration and functioning as one of said oxygen sensor pair.

7. The glucose sensor of claim 5 including means therein to sense the temperature level of the body fluids and to adjust the output differential of the pair of oxygen sensors for the temperature at which measurement is made.

8. The glucose sensor of claim 5 wherein said oxygen sensors are electrodes and their adjusted current output differential constitutes the glucose content measurement.

* * * * *